(12) United States Patent
Ozawa et al.

(10) Patent No.: US 8,158,423 B2
(45) Date of Patent: Apr. 17, 2012

(54) METHOD OF MAKING A HAIR

(75) Inventors: Hidehiro Ozawa, Nagano (JP); Mariko Yamaki, Nagano (JP); Makoto Asashima, Tokyo (JP); Satoshi Ebina, Nagano (JP)

(73) Assignee: Matsumoto Dental University, Shiojiri-Shi, Nagano (JP)

( * ) Notice: Subject to any disclaimer, the term of this patent is extended or adjusted under 35 U.S.C. 154(b) by 154 days.

(21) Appl. No.: 12/525,983

(22) PCT Filed: Feb. 5, 2008

(86) PCT No.: PCT/JP2008/051848
§ 371 (c)(1), (2), (4) Date: Aug. 5, 2009

(87) PCT Pub. No.: WO2008/096745
PCT Pub. Date: Aug. 14, 2008

(65) Prior Publication Data
US 2010/0304479 A1 Dec. 2, 2010

(30) Foreign Application Priority Data

Feb. 6, 2007 (JP) ................................. 2007-027390

(51) Int. Cl.
*C12N 15/02* (2006.01)
(52) U.S. Cl. .......................... 435/377; 435/384; 435/387
(58) Field of Classification Search ........................ None
See application file for complete search history.

(56) References Cited

OTHER PUBLICATIONS

Imamura et al. Embryonic Stem Cell-Derived Embryoid Bodies in Three-Dimensional Culture System Form Hepatocyte-Like Cells in Vitro and in Vivo. Tissue Egineering, 2004, vol. 10, pp. 1716-1724.*
Morgan et al. Feasibility Study of the Potential for Human Exposure to Pet-Borne Diazinon Residues Following Lawn Applications. Bull Environ. Contam. Toxicol., 2001, vol. 66, pp. 295-300.*
Li et al. Pluripotent Stem Cells from the Adult Mouse Inner Ear. Nature Medicine, 2003, vol. 9, 1293-1299.*
Mitsui et al. Genes for a range of growth factors and cyclin-dependent kinase inhibitors are expressed by isolated human hair follicles British J, Dermatology, 1997, vol. 137, pp. 693-698.*
Rebecca J. Morris[1,5], et al; "Capturing and profiling adult hair follicle stem cells", Nature Biotechnology, 2004, vol. 22, No. 4, pp. 411-417.
Jose B. Cibelli [1] et al; "Parthenogenetic Stem Cells in Nonhuman Primates", Science, 2002, vol. 295, p. 819 (Fig. 1F).
Motonobu Nakamura; "Mono Saisei eno Seibutsugaku", Nihon Hifuka Gakkai Zasshi, 2004, vol. 114, No. 3, p. 416-417 (p. 417).
Claudia Bagutti, et al; "Differentiation of Embryonal Stem Cells into Keratinocytes: Comparision of Wild-Type and $\beta_1$ Integrin-Deficient Cells", Developmental Biology 179, 184-196 (1996) (Materials and Methods, Fig. 1).
Stuart H. Yuspa, et al; "Regulation of Hair Follicle Development: An In Vitro Model for Hair Follicle Invasion of Dermis and Associated Connective Tissue Remodeling", J. Investigative Dermatology, 1993, vol. 101, p. 27S-32S.
Tammy-Claire Troy, et al; "ES Cell Differentiation Into the Hair Follicle Lineage in Vitro", Methods in Molecular Biology, vol. 185, p. 255-260, 2002.
Report of "Reserch of Organ Regeneration, and Survey on Feasible Medical and Economical Effects", Oct. 2006, Toray Corporate Business Research, Inc.
Una Chen,et al; "Differentiation of Mouse Embryonic Stem Cells In Vitro: III. Morphological Evaluation of Tissues Developed After Implantation of Differentiated Mouse Embryoid Bodies", Developmental Dynamics: An Official Publication of the American Association of Anatomists, Jul. 1993 LNKD- PUBMED:8219361, vol. 197, No. 3, Jul. 1993, pp. 217-226, XP002612676, ISSN: 1058-8388, p. 218, left-hand column, paragraph 2-right-hand column, paragraph 2, p. 224, left-hand column- p. 224, right-hand column, paragraph 1.
Toray Corporate Business Research Inc,; Report of "Study on organ regeneraton research and feasible medical and economic effects", Oct. 2006, 2 pages.

* cited by examiner

*Primary Examiner* — Deborah Crouch
(74) *Attorney, Agent, or Firm* — Ladas & Parry LLP

(57) ABSTRACT

A method of making a hair, including a step of culturing an undifferentiated cell of a mammal to produce an embryoid body and a step of further culturing the embryoid body is provided, wherein the culturing step is to culture the embryoid body on a three-dimensional matrix for 5 to 12 days. Furthermore, a biological material obtainable by the method of making a hair as described above is provided. Moreover, a biological material for a screening system of evaluating a medical product or the like, obtainable by utilizing the method of making a hair as described above is provided.

2 Claims, 6 Drawing Sheets

METHOD OF MAKING A HAIR

TECHNICAL FIELD

The present invention relates to a method of making a hair and a biological material.

BACKGROUND ART

Regeneration of hair, namely, hair growth, is a topic of great interest for not only middle-aged and elderly people but also young people recently, and westernization of life style, including food, has been pointed out as a reason for hair loss among young people. Furthermore, interest in hair growth has become greater than ever from the viewpoint of improvement of the quality of life (QOL) which has been rapidly being of increased concern to middle-aged and elderly people with the aging of society. While the market for hair growth agents in Japan has been 30 billion yen as of 2005, this market size is unnaturally smaller than its potential size because the effect of commercially available hair growth agents has not been significant at present, but it is estimated that, if a reliable hair growth agent whose drug efficacy can be proven scientifically is developed, the market size for hair growth agents would be up to 200 billion yen in Japan, and even 2,000 billion yen worldwide (see "Research of Organ Regeneration Studies and their Feasible Medical and Economical Effect" (October 2006)). Thus, it is possible to say that at present society demands development of a reliable hair growth agent.

The fact that the effect of hair growth agents that are commercially available at present is not significant is due to the simple reason that the only evaluation methods at present utilize living animal and no proper evaluation system for evaluating a hair growth effect efficiently and globally is present. That is, because "a screening system for evaluating the effect of a hair growth agent globally and efficiently in vitro" is not present, a domestic market of potentially 200 billion yen has remained at 30 billion yen. Meanwhile, pharmaceutical companies commonly evaluated several tens of thousands to several millions of drugs at a high speed in conformity with their own procedures or joint development agreement by exploiting such a general drug development screening system, and as a result, drugs with excellent effects and safety have been developed. However, the development of hair growth agents has substantially deviated from the state of such common drug development. Minoxidil (Japanese name: Riup), which is currently the most reliable hair growth agent in the world, was originally developed as a therapeutic drug for a circulatory organ but has a history that its development was discontinued due to its severe side effects. However, a phenomenon of excessive hair growth was significantly found in an investigated subject in the course of a clinical investigation, and it was exploited as a hair growth agent but not as an original therapeutic drug for a circulatory organ. Although minoxidil was by chance found to be a hair growth agent with excellent results, nevertheless, a common understanding in the world is that the hair growth effect of minoxidil is not necessarily at a satisfactory level. Furthermore, a hair growth agent that was developed while focusing attention on the hair growth inhibiting function of an androgen has also been commercially available but its hair growth effect has not necessarily been highly appreciated. These facts mean that development of a hair growth agent has been conducted inefficiently, and if a process corresponding to that of usual drug development is possible, it would be possible to develop a more effective hair growth agent with excellent safety.

Meanwhile, it is thought that gray hair is caused by deterioration of the melanosome production function of a melanocyte for producing melanotic pigment (melanosome) due to its aging, or deterioration of the function of delivering melanosome produced by a melanocyte to a trichoblast for some reason(s), or deterioration of the melanosome-capturing function of a trichoblast. Regardless of the cause of gray hair, no method of recovery of original color of a gray hair has been present at all in the world at present. Whereas hair growth is principally of great importance for men, gray hair is of great importance not only for men but also for women.

Furthermore, reference will be made to fur as a material to make warm clothing in association with a hair growth technique. Conventionally, fur has a high utility value as a material to make warm clothing but its utilization has been challenged from the recent prevalence of the viewpoint of animal protection. However, no material of such high functionality to make warm clothing and replace fur presently exists. Therefore, if a technique for producing fur without killing an animal existed, it would be a start to resolving this problem.

DISCLOSURE OF THE INVENTION

Problems to be Solved by the Invention

One of the objects of the present invention is to provide a novel method of making a hair.

Another object of the present invention is to provide a novel biological material.

Means for Solving the Problem

A first aspect of the present invention is a method of making a hair, including a step of culturing an undifferentiated cell of a mammal to produce an embryoid body and a step of further culturing the embryoid body, wherein the culturing step is to culture the embryoid body on a three-dimensional matrix for 5 to 12 days.

A second aspect of the present invention is a biological material obtainable by the method of making a hair according to the first aspect of the present invention.

A third aspect of the present invention is a biological material for a screening system of evaluating a medical product or the like, obtainable by utilizing the method of making a hair according to the first aspect of the present invention.

Advantageous Effect of the Invention

According to the first aspect of the present invention, it is possible to provide a novel method of making a hair.

According to the second or third aspect of the present invention, it is possible to provide a novel biological material.

BEST MODE FOR CARRYING OUT THE INVENTION

Figure 1:
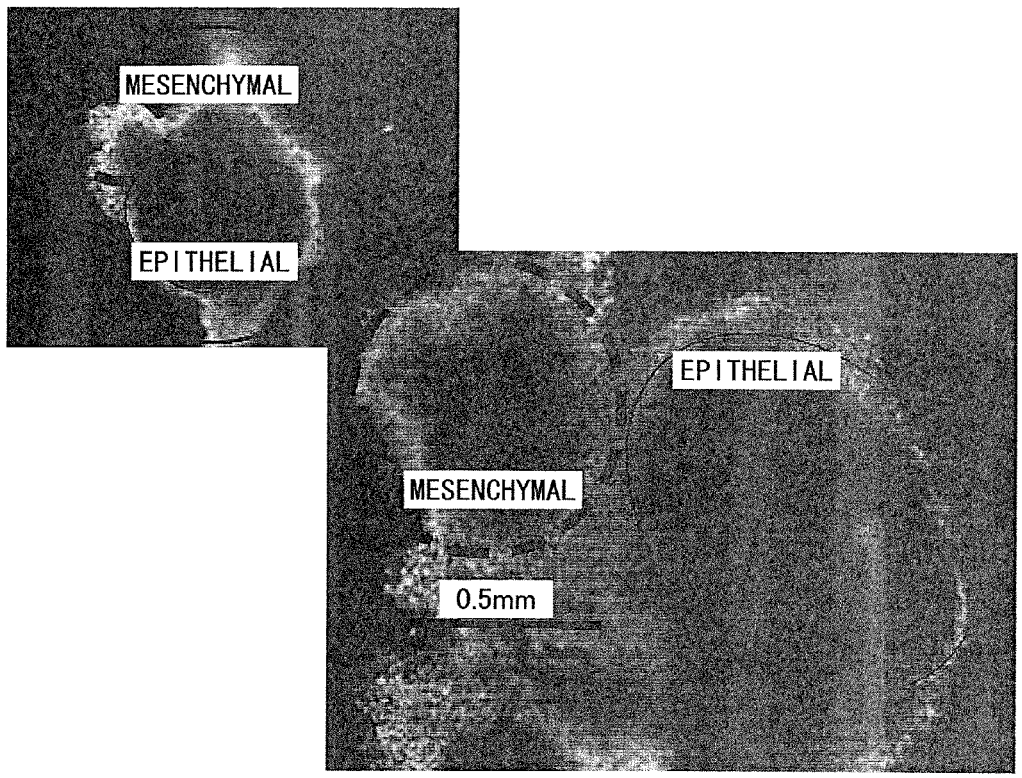
FIG. 1 is a diagram illustrating a tooth germ of a mandibular molar tooth of a fetal mouse.

An embodiment of the present invention relates to a method of making a hair, more particularly it relates to a method of making a hair in which an embryoid body obtained by culturing an undifferentiated cell of a mammal is further cultured by using a carrier, and furthermore, relates to production of fur and development of a medical product such as a hair growth agent, utilizing the method.

Therefore, an embodiment of the present invention aims to provide a novel method of making a hair in which an embryoid body is produced by culturing an undifferentiated cell of a mammal and the produced embryoid body is further cultured three-dimensionally.

Furthermore, an embodiment of the present invention aims to utilize the method to produce fur, and provide a biological material for a screening system of evaluating a medical product or the like.

A method of making a hair according to an embodiment of the present invention is a method of making a hair composed of a step of culturing an undifferentiated cell of a mammal to produce an embryoid body and a step of further culturing the embryoid body, characterized in that the culturing step is to culture the embryoid body on a three-dimensional matrix for 5 to 12 days.

Also, in the method of making a hair according to an embodiment of the present invention, it is preferable that the three-dimensional matrix for culturing the embryoid body is a carrier for culturing or transplantation, and in particular, it is preferable that the carrier is a type-I collagen scaffold.

Also, it is preferable that the undifferentiated cell is further cultured in a culture medium containing an inducing factor, and in particular, it is preferable that the inducing factor includes all of insulin growth factor 1, fibroblast growth factor 2, and transforming growth factor β1.

It is preferable that the undifferentiated cell is further mixed and cultured with an ES cell.

Also, the mammal is one kind selected from all the mammals.

Furthermore, an embodiment of the present invention provides a biological material obtainable by the method of making a hair as described above, and in particular, which is characterized in that the biological material is fur of an animal.

Moreover, an embodiment of the present invention is also characterized in that a biological material obtainable by the method of making a hair as described above is utilized as a biological material for a screening system of evaluating a medical product such as a hair growth agent.

According to an embodiment of the present invention, it is possible to provide a novel method of making a hair in which an undifferentiated cell of a mammal is cultured to produce an embryoid body and the produced embryoid body is further cultured three-dimensionally.

Furthermore, it is possible for an embodiment of the present invention to provide fur produced by a method of making a hair according to an embodiment of the present invention.

Furthermore, it is possible to provide a biological material for a screening system of evaluating a hair growth agent and the like, due to a biological material obtained by utilizing a method of making a hair according to an embodiment of the present invention.

Moreover, there is a possibility that it is possible to provide a regenerative medical approach exploiting a regeneration function of an organism, such as a biological material produced by a method of making a hair according to an embodiment of the present invention being implanted into a scalp and sutured to attain complete regeneration of hair.

Next, one preferred embodiment of the present invention will be described in detail but the present invention is not limited to it.

One embodiment of the present invention is characterized in that a novel method of making a hair is arrived at by using an undifferentiated cell which has the ability to differentiate into a wide variety of cells and/or tissues in a mammal, so as to produce an embryoid body and further culturing the produced embryoid body three-dimensionally.

Therefore, a method of making a hair according to an embodiment of the present invention is characterized in that it is composed of a combination of "a step of culturing an undifferentiated cell of a mammal to produce an embryoid body" and further "a step of culturing the produced embryoid body on a three-dimensional matrix".

A preferred embodiment of the present invention will be described in more detail below, while referring to the drawings.

First, an undifferentiated cell to be used in an embodiment of the present invention will be described. An undifferentiated cell associated with an embodiment of the present invention is a cell having a capability of transforming, namely, differentiating, into a particular cell, when an instruction to transform into a cell is received. Furthermore, the cell also has a capability of replicating or regenerating itself for a long period of time during its undifferentiated state before achieving its transformation. There is a hierarchy amongst undifferentiated cells, wherein a more undifferentiated stem cell has a high self-replicating-capability and has the ability to differentiate into a very wide range of cell lines, but an inferior stem cell may lose its self-replicating-capability so that cell lines into which it has the ability to differentiate may be limited. An ES cell is an undifferentiated cell which is in a higher rank next to a fertilized egg. In an organ of a mammal, a tissue-specific undifferentiated cell (that is, a somatic stem cell, also known as a tissue stem cell) is present. It is thought that a somatic stem cell has a capability of differentiating into a specific type of cell, and a cell having the same capability as that of itself is regenerated (self-replication) on its division, thereby maintaining each tissue. That is, it is possible to isolate an embryonic stem cell, namely, an ES cell, from an embryo, a somatic stem cell from an adult, and an embryo germ cell from a fetus.

In particular, an ES cell is known as a cell that self-replicates semipermanently while retaining its undifferentiated state under a certain culturing condition and has totipotency or multipotency whereby it is possible to differentiate into any kind of cell including a germ cell line.

An ES cell is isolated from a fertilized embryo, that is, the initial stage of an embryo during which a fertilized egg differentiates and evolves into a fetus, and is also called a multipotent stem cell because it has a capability of growing into any types of cell in a body. An ES cell has been studied for a "raw material" capable of creating each kind of cell which is to replace a cell, tissue or organ whose function has been lost by an accident or disease, because while it is isolated from an inner layer cell (inner cell mass) of a blastocyst at 5 or 6 days after its fertilization and cultured, it is possible to increase infinitely by means of culturing in a laboratory, contrary to a somatic stem cell isolated from a human body, and it has a universality such that it is possible to transform into any types of cell. Theoretically, a method for transplanting an organ without causing rejection is also thought possible wherein a cell differentiated from an ES cell is recombined with an immunological gene by using a technique of gene therapy, or an embryo having genetic information of a subject is created, and an ES cell is isolated therefrom and induced to become an intended cell.

Meanwhile, a somatic stem cell refers to a cell at a state before its differentiation which is isolated from tissue already formed in a body. In tissue, many cells which have particular functions in the tissue and have already experienced differentiation are present, and among these, an undifferentiated cell before its differentiation into a cell having such a particular function, namely, a stem cell, is mixed and present. A somatic stem cell has a capability of replicating and producing a cell identical to itself and it is possible by means of its differentiation to create any individual cell in tissue in which it is present.

A representative example is, for example, a bone marrow stem cell which has already been exploited for many therapeutic treatments because the particular type of tissue into which it differentiates is known, and which is used for bone marrow transplantation necessary for therapy of leukemia or the like.

Therefore, it is possible to achieve an embodiment of the present invention, when an undifferentiated cell having a function as described above is used.

In a preferred embodiment of the present invention, a tooth germ mesenchymal cell of a fetal mouse at 14 days of age (ED14) was used so as to have its function of controlling its differentiation into an epithelial cell. However, an undifferentiated cell to be used is not limited to a tooth germ mesenchymal cell and any one kind of all the undifferentiated cells having multipotency, such as a somatic stem cell and a bone marrow stem cell may be used.

In a preferred embodiment of the present invention, after tooth germ from mandibular molar teeth of 12 white fetal mice (ddy) at 14 days of age (ED14) was sampled and the tissue was washed in a Hanks' solution, and subjected to Disperse enzyme treatment on ice for 5 hours, the mesenchymal tissue was isolated under a microscope (in FIG. 1, a part indicated by a solid-line circle, a part indicated by a dotted-line circle, and a part indicated by a solid-line ellipse indicate the entirety of a tooth germ, a mesenchymal cell, and an epithelial cell, respectively).

Figure 2A:
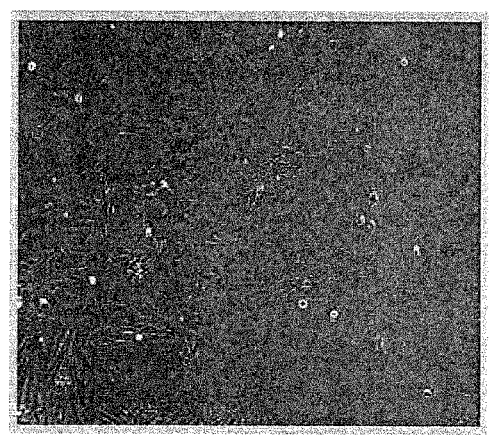
FIG. 2A is a diagram illustrating a mesenchymal cell derived from a tooth germ of a fetal mouse, which indicates culturing of the mesenchymal cell.

After centrifugal washing of the mesenchymal tissue at 12,000 rpm for 3 minutes, sediment was transferred to a 10-cmϕ plastic dish and cultured on a 10% FBS-added α-MEM medium (fetal bovine serum, FBS medium) at 37° C. under 5% $CO_2$ for 1 day. The next day, the medium was replaced with an MSCGM medium (Chambrex), and similarly, culturing was conducted at 37° C. under 5% $CO_2$ (FIG. 2A). Subsequently, a stabilized mesenchymal cell line was created by means of subculture before confluent growth began. This cell line will be called MDU1 below.

Figure 2B:
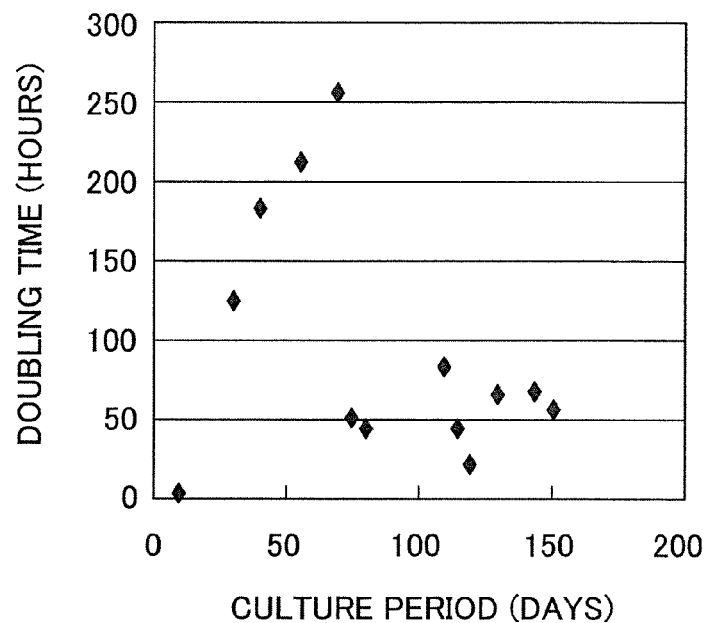
FIG. 2B is a diagram illustrating a mesenchymal cell derived from a tooth germ of a fetal mouse, which indicates the growth rate of a culture.
Figure 2C:
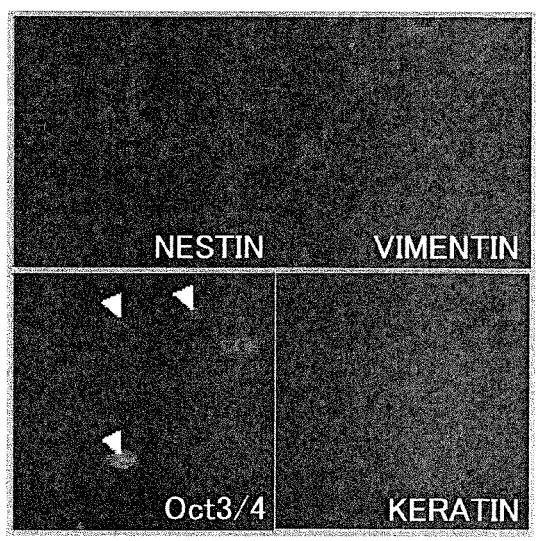
FIG. 2C is a diagram illustrating a mesenchymal cell derived from a tooth germ of a fetal mouse, which indicates expression of marker proteins.

Although deterioration of the capability of this cell line to divide was found temporarily when 20 days of culturing had passed, cell division actively commenced again when 30 days had passed, and subsequently, a cell line that had the ability to subculture stably was obtained. The growth rate of a cultured cell was stable when about 120 days had passed, and the cell divided once per about every 50 hours (FIG. 2B). An MDU1 cell line expressed nestin or OCT 3/4 which is a marker of undifferentiation as illustrated in FIG. 2C, and therefore, had a property of considerable undifferentiation. Furthermore, it includes a few epithelial cells and is mostly mesenchymal cells because it is vimentin-positive and keratin-negative (note: FIG. 2C indicates that nestin and vimentin were expressed in cytoplasm while Oct 3/4 was expressed in a cell nucleus and this cell line was positive for nestin and Oct 3/4 which were markers of undifferentiation and positive for vimentin which was a marker of a mesenchymal cell. Furthermore, this cell line was negative for keratin because it was not expressed in cytoplasm which was a marker of an epithelial cell.)

Figure 3:
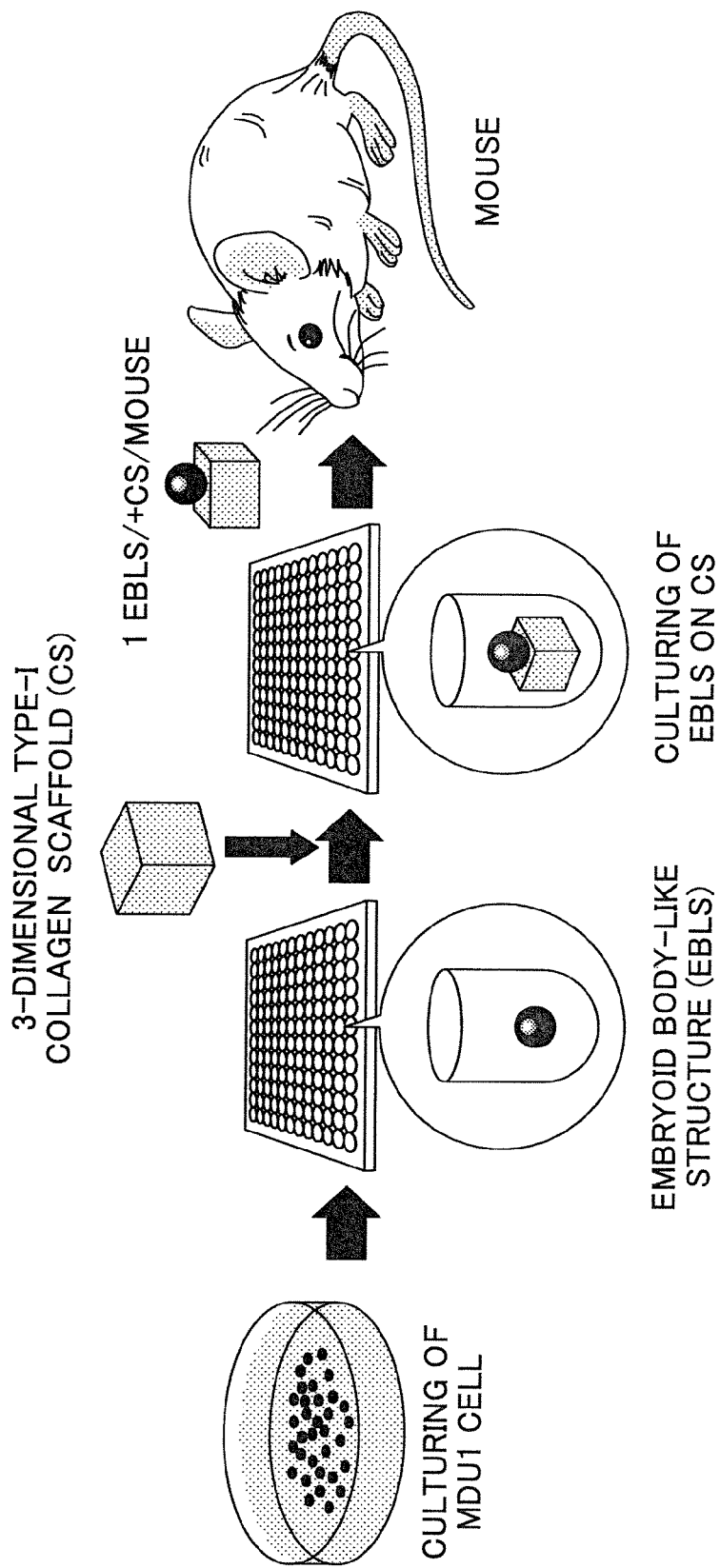
FIG. 3 is a schematic diagram illustrating a method of making a hair according to an embodiment of the present invention.

Then, the MDU1 cell line was released from the plastic dish by means of trypsin-EDTA treatment (GIBCO), recovered, and broken through a plastic filter, and then, its seeding was conducted onto a 96-well low adhesion plastic plate (Nunc) to produce an embryoid body-like structure (embryoid body-like sphere). The produced embryoid body-like structure was cultured for 5-12 days together with a collagen carrier (Collagen Sponge Honeycomb™, KOKEN CO., LTD.: collagen scaffold (CS)) having been finely-cut into about a 1 mm×1 mm×1 mm size. It took 5 days to bond all of the cells to the CS, and when no hair was produced by 12 days, no hair was produced even when culturing continued for 3 weeks or more. As a result, it is recognized that culturing for 5-12 days is preferable in an embodiment of the present invention. A part of the CS to which the embryoid body-like structure was bonded, was fixed without change and observed as a paraffin-covered sample. The remaining samples were transplanted into the cranial epithelium and back muscle fascia of an adult mouse (ddy) at 6 weeks of age by means of a common practice, and sampled and observed by a light microscope after 15 days. FIG. 3 illustrates the protocol of the above-described embodiment of the present invention.

[Verification of Hair Making]
[Verification in Vitro]

Figure 4:
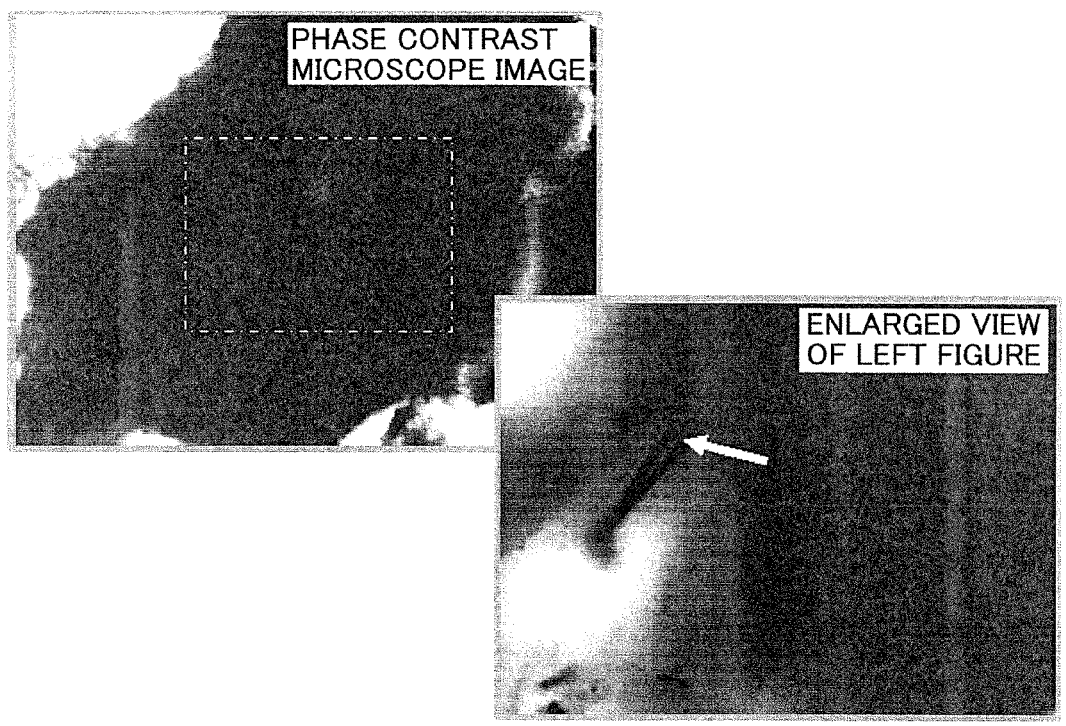
FIG. 4 is a diagram illustrating a black hair having grown in vitro.
Figure 5:
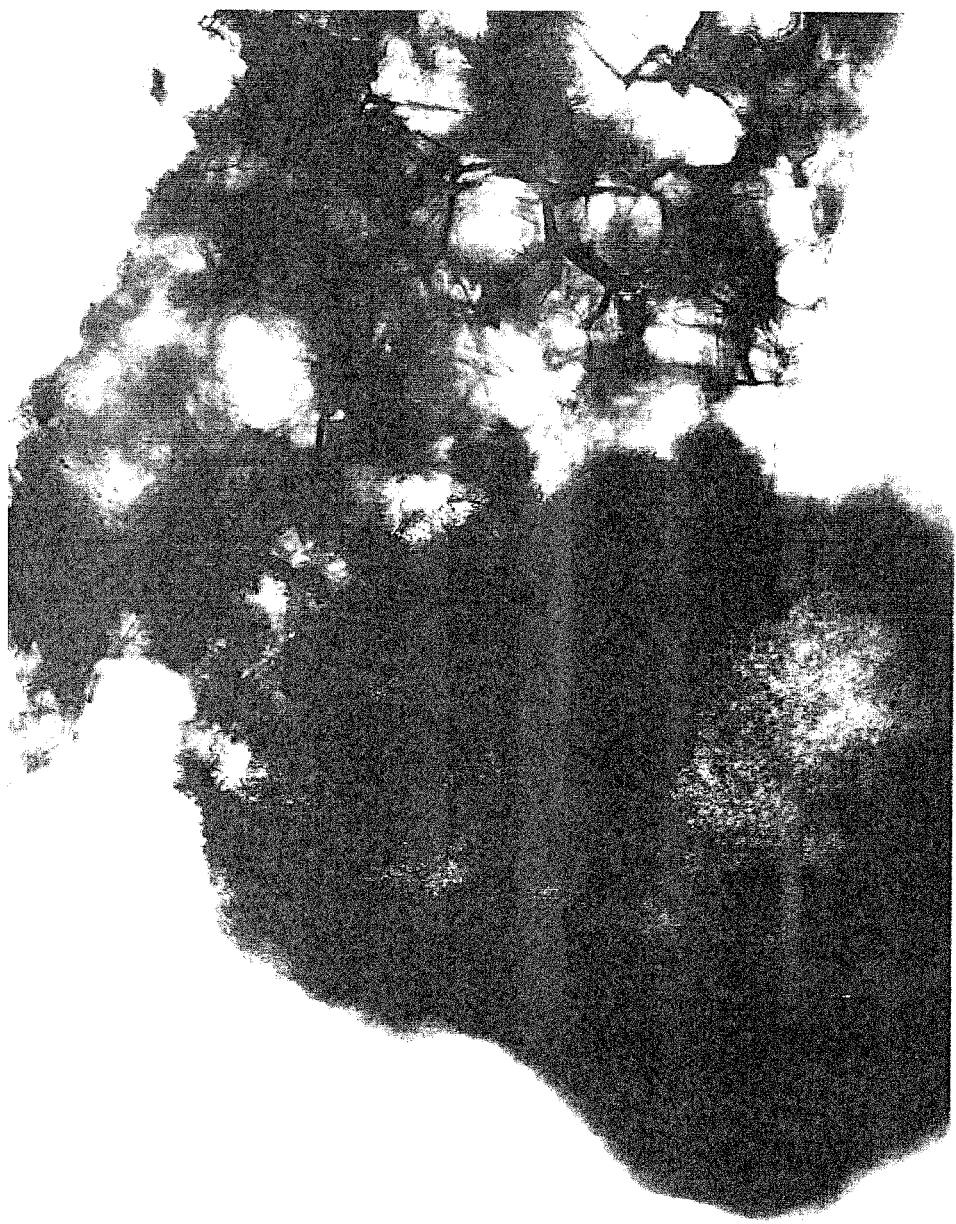
FIG. 5 is a diagram illustrating making of a black hair in vitro, utilizing an ES cell.

First, the state of making a hair in vitro was verified (FIG. 4). A black hair had been grown on the CS to which the embryoid body-like structure was bonded (a typical example is indicated by an arrow). That is, it was confirmed that not only was it possible to make a hair but also it was possible to form a melanocyte, and further it was possible to make a hair containing a melanosome produced by melanocyte, in this culture system. Because the MDU1 cell line was derived from a white mouse, it was verified that a melanocyte was newly formed in this system. When a culture medium containing a growth factor was used and an MDU1 cell line was cultured similarly, insulin growth factor 1 (insulin growth factor-1, IGF-1; TOYOBO), fibroblast growth factor 2 (fibroblast growth factor-2, FGF-2; TOYOBO), and transforming growth factor β1 (transforming growth factor-β1, TGF-β1; TOYOBO) facilitated growth of a hair significantly. Furthermore, when the MDU1 cell line was not singly cultured but was mixed with an embryonic stem cell (ES cell) derived from a mouse and cultured similarly (wherein a culture in which the MDU1 was mixed with the ES cell is called a chimeric embryoid body), this also facilitated growth of a hair significantly. Moreover, it was confirmed that a hair was made even when culturing was not conducted for any of the MDU1 cell line and the chimeric embryoid body, but was conducted for a single embryonic stem cell (ES cell) similarly to that of the above-described practical example or culturing was conducted similarly while no inducing factor was included (FIG. 5).

Furthermore, it was confirmed that when a single embryonic stem cell (ES cell) was cultured on a 10% serum (FCS)-added medium (wherein no inducing factor is included) through the entire process, the efficiency of hair induction was increased from about 10% to about 15%.

[Verification in Vivo]

Figure 6:
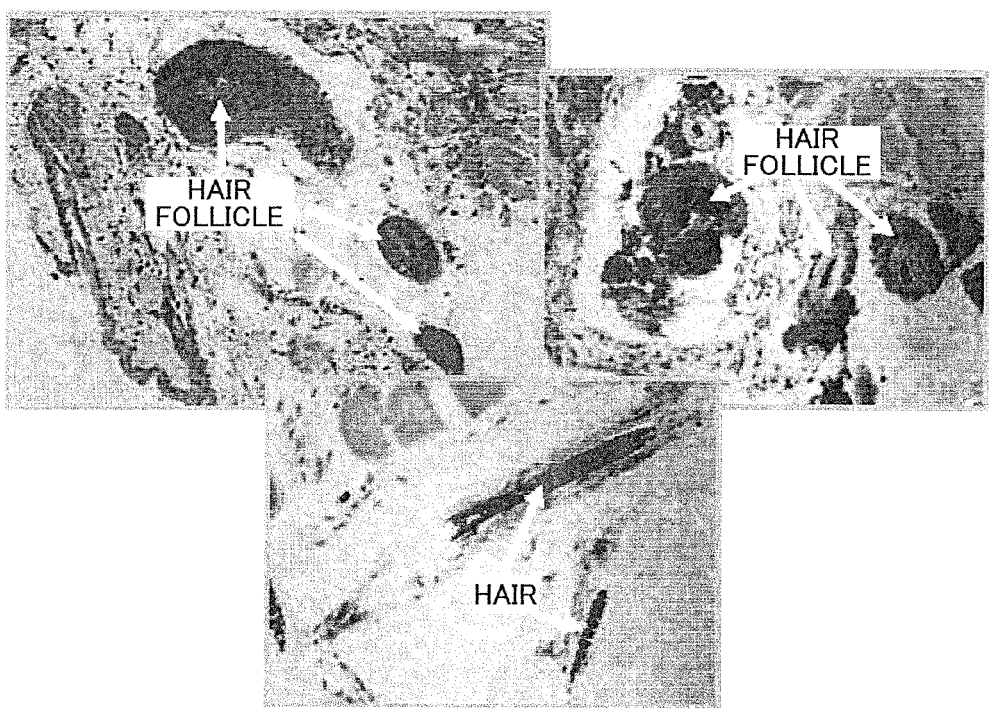
FIG. 6 is a microscope image indicating growth of a black hair of a mouse and its hair follicle in vivo.

Then, collagen carriers to which the cultured chimeric embryoid body had been adsorbed were transplanted into the cranial epithelium and back muscle fascia of a mouse by means of a common practice, were sampled and observed by a light microscope after 15 days. As a result, it was verified that a hair was made in a mouse in vivo (FIG. 6). The hair made herein was a black hair similar to the hair made in vitro. Furthermore, a hair follicle was also frequently found, which is an organ producing a hair, and certainly, it was verified that a hair was newly made by this method.

Additionally, although an embryoid body was produced from a mesenchymal cell derived from a tooth germ of a fetal mouse and further cultured three-dimensionally whereby it was possible to make a hair in the present practical example, an embodiment of the present invention is not limited to a mouse, is generally feasible for mammals, and is applicable to regeneration of a hair of mammals including a human being. Furthermore, an undifferentiated cell to be used in an embodiment of the present invention is not limited to a mesenchymal cell, and all kinds of the undifferentiated cells are applicable to an embodiment of the present invention. Moreover, it is also possible to provide a biological material of a screening system for evaluation of a medical product such as a hair growth agent, due to a biological material obtainable by utilizing a method of making a hair according to an embodiment of the present invention.

Although the preferred embodiments and practical examples of the present invention have been specifically described above, an embodiment of the present invention is not limited to such specific embodiments or practical examples, and various alterations/modifications thereof are possible within the scope of the present invention as described in the claims.

APPENDICES

Appendix (1): A method of making a hair composed of a step of culturing an undifferentiated cell of a mammal to produce an embryoid body and a step of further culturing the embryoid body, wherein the method of making a hair is characterized in that the culturing step is to culture the embryoid body on a three-dimensional matrix for 5 to 12 days.

Appendix (2): The method of making a hair as described in appendix (1), characterized in that the three-dimensional matrix for culturing the embryoid body is a carrier for culturing or transplantation.

Appendix (3): The method of making a hair as described in appendix (2), characterized in that the carrier is a type-I collagen scaffold.

Appendix (4): The method of making a hair as described in any one of appendices (1) to (3), characterized in that the undifferentiated cell is further cultured in a culture medium containing an inducing factor.

Appendix (5): The method of making a hair as described in appendix (4), characterized in that the inducing factor includes all of insulin growth factor 1, fibroblast growth factor 2, and transforming growth factor $\beta 1$.

Appendix (6): The method of making a hair as described in any one of appendices (1) to (5), characterized in that the undifferentiated cell is further mixed and cultured with an ES cell.

Appendix (7): The method of making a hair as described in any one of appendices (1) to (6), characterized in that the mammal is one kind selected from all the mammals.

Appendix (8): a biological material obtainable by the method of making a hair as described in any one of appendices (1) to (7).

Appendix (9): The biological material as described in appendix (8), characterized in that the biological material is fur of an animal.

Appendix (10): a biological material for a screening system of evaluating a medical product or the like, obtainable by utilizing the method of making a hair as described in any one of appendices (1) to (7).

The present application claims the benefit of its priority based on Japanese Patent Application No. 2007-027390 filed on Feb. 6, 2007, the entire contents of which are hereby incorporated by reference.

INDUSTRIAL APPLICABILITY

According to an embodiment of the present invention, it is possible to develop an unprecedented and effective hair growth agent, and further it is also possible to develop a drug allowing a gray hair to recover to a hair of its original pigment color. In addition, according to an embodiment of the present invention, it is possible to develop a technique for producing fur without killing an animal. Moreover, an embodiment of the present invention has a possibility that a biological material produced thereby is implanted into a scalp so that it is possible to conduct complete regeneration of hair. Thus, the industrial utility value of an embodiment of the present invention is very high from the viewpoint of its market size and high amount of social interest.

The invention claimed is:

1. A method of making a hair comprising:
culturing a mammalian stem cell in a culture medium comprising an inducing factor, wherein the inducing factor comprises insulin growth factor 1, fibroblast growth factor 2, and transforming growth factor $\beta 1$ to produce an embryoid body-like structure;
culturing the embryoid body-like structure on a three-dimensional matrix for 5 to 12 days, wherein the three-dimensional matrix is a carrier for culturing or transplantation; and
further culturing the embryoid body,
wherein hair develops.

2. A method of making a hair comprising:
culturing a mammalian stem cell and an ES cell in a culture medium comprising an inducing factor, wherein the inducing factor comprises all of insulin growth factor 1, fibroblast growth factor 2, and transforming growth factor $\beta 1$ to produce a chimeric embryoid body-like structure; and
culturing the chimeric embryoid body-like structure on a three-dimensional matrix for 5 to 12 days, wherein the three-dimensional matrix for culturing the embryoid body is a carrier for culturing or transplantation,
wherein hair develops.

* * * * *